United States Patent [19]

Rademacher et al.

[11] Patent Number: 4,719,294

[45] Date of Patent: Jan. 12, 1988

[54] ISOLATION OF UNREDUCED OLIGOSACCHARIDES

[75] Inventors: Thomas W. Rademacher; Raymond A. Dwek, both of Oxford, United Kingdom

[73] Assignee: Monsanto Company, St. Louis, Mo.

[21] Appl. No.: 772,988

[22] Filed: Sep. 6, 1985

[51] Int. Cl.[4] .................... C07H 19/00; C07H 21/00
[52] U.S. Cl. .................................. 536/22; 536/18.7; 536/123
[58] Field of Search .................. 536/123, 22, 18.7

[56] References Cited

U.S. PATENT DOCUMENTS 4,362,720 12/1982 Lemieux et al. .................. 536/18.7

OTHER PUBLICATIONS

Takasaki et al., Meth. Enzymol. 83, 263–268 (1982).
Yamashita et al., Ibid.; 105–126 (1982).
Mellis et al., Anal. Biochem. 114, 276–280 (1980).
Mizuochi et al., J. Biol. Chem. 251, 7404–7409 (1978).
Homans et al., Biochim. Biophys. Acta, 760, 256–261 (1983).
Homans et al., Proc. Natl. Acad. Sci. USA, 81, 6286–6289 (1984).

Primary Examiner—Ronald W. Griffin
Attorney, Agent, or Firm—Scott J. Meyer; James W. Williams, Jr.

[57] ABSTRACT

A preparative scale method for the isolation of unreduced oligosaccharides of glycoproteins and glycohormones having an N-linked oligosaccharide structure is disclosed. The method employs hydrazinolysis of the glycoprotein or glycohormone under reaction conditions to cause cleavage at the N-linked sites, producing a mixture having as a major component a de-N-acetylated hydrazone derivative of the oligosaccharides, followed by N-acylation of the hydrazone derivative, acid-catalysis of the hydrazone derivative to produce unreduced oligosaccharides, and subjecting the resulting unreduced oligosaccharides to cellulose column chromatography to remove contaminants and to recover the unreduced oligosaccharides.

17 Claims, 7 Drawing Figures

ISOLATION OF UNREDUCED OLIGOSACCHARIDES

BACKGROUND OF THE INVENTION

This invention relates to a method for the isolation of unreduced oligosaccharides from glycoproteins and glycohormones having an N-linked oligosaccharide structure.

The isolation of oligosaccharides from glycoproteins and glycohormones is of great interest for a number of reasons. First, it is of primary importance in the structural analysis of the carbohydrate moieties of the parent glycoproteins and glycohormones. These materials are known to contain several sugar chains in the molecule or microheterogeneity in single sugar chains. Therefore, it is necessary to fractionate these chains before structural analysis can be carried out.

Isolated oligosaccharides also are useful per se for preparing neoglycoproteins by attachment of individual oligosaccharides to various peptide or protein chains.

Hydrolytic digestion with enzymes, e.g. bacterial proteases such as Pronase ®, has long been a method of cleaving glycoproteins to obtain glycopeptides, but is generally unsatisfactory for various reasons including incomplete digestion and difficulties in fractionation of the resulting mixtures.

Chemical methods have also been employed to liberate free oligosaccharides from glycoproteins. A preferred chemical method involves hydrazinolysis which was originally described by Matsushima and Fujii, *Bull. Chem. Soc. Jpn.* 30, 48 (1959), and later developed by Bayard and Montreuil, "Methodologie de la Structure et du Métabolisme des Glycoconjugûes," pp. 208–18, CNRS, Paris, 1974. According to the latter published procedure, the glycoprotein was heated with anhydrous hydrazine for 30 hours followed by treatment with nitrous acid to fragment the oligosaccharides. No attempt was made to recover intact oligosaccharides.

The hydrazinolysis method was further refined by Takasaki, Mizuochi and Kobata, *Meth. Enzymol.* 83, Academic Press, 1982, pp. 263–8. These investigators subjected the hydrazinolysis product to N-acetylation with acetic anhydride in saturated $NaHCO_3$ solution followed by exchange of the $Na^+$ with $H^+$ ions by passage over a Dowex ® 50 cation exchange resin. The N-acetylglucosamine residues were then subjected to paper chromatography using butanol:ethanol:water (4:1:1) and, after reduction with sodium borotritide ($NaB^3H_4$) in NaOH, were subjected to another paper chromatographic step using ethyl acetate:pyridine:acetic acid:water (5:5:1:3). The released sugars were finally subjected to high resolution gel-permeation chromatography with Bio-Gel ® P-4 to obtain an oligosaccharide profile as further described by Yamashita, Mizuochi and Kobata, Ibid., pp. 105–126. The Takasaki et al method, however, produces a mixture of degraded components containing reduced alditols. The reduction causes the production of radiolabeled reduced alditols, e.g. tritium-labeled N-acetylglucosaminitol or N-acetylmannosaminitol. According to Mellis and Baenziger, *Anal. Biochem.* 114, 276–280 (1981), the latter products are produced by alkali induced epimerization at the C-2 position of the amino-sugar at the reducing terminus. Such reduced alditols are not suitable for further reactions.

Although the Takasaki et al. method is useful for structural analysis of glycoproteins, the published procedure is not practical for a preparative scale isolation of unreduced oligosaccharides. It also results in substantial loss of sialic acid residues.

BRIEF DESCRIPTION OF THE INVENTION

The method of isolating unreduced oligosaccharides from glycoproteins and glycohormones according to the present invention comprises:

(a) hydrazinolyzing the glycoprotein or glycohormone by heating an essentially water-free, essentially salt-free glycoprotein or glycohormone in the presence of essentially water-free hydrazine under reaction conditions sufficient to cause cleavage at the N-linked sites to produce a mixture having as a major component a de-N-acetylation hydrazone derivative of an oligosaccharide;

(b) N-acylating the hydrazone derivative of (a) with a desired acylating agent to form a N-acylated hydrazone derivative of oligosaccharide;

(c) subjecting the hydrazone derivative of (b) to acid catalysis to produce said unreduced oligosaccharides; and (d) subjecting the unreduced oligosaccharides of (c) to cellulose column chromatograph to remove contaminants and recover therefrom said unreduced oligosaccharides.

The method of the present invention is applicable to a wide variety of glycoproteins and glycohormones which are ubiquitous components of nature, being found in extra- and intracellular fluids, connective tissues and cellular membranes. Purified glycoproteins and glycohormones can be used as well as crude extracts and fractions of oligosaccharide-containing source materials. Thus, the starting materials for the hydrazinolysis can be derived from materials such as, for example, (1) Purified glycoproteins and glycohormones;
(2) Whole serum and its fractions;
(3) Biological secretions such as, for example, urine, milk, meconium, mucus, and the like substances;
(4) Whole organs, for example, kidneys, liver, heart, spleen, pancreas, lung;
(5) Plant stem and leaf extracts;
(6) Seed material;
(7) Lectins; and
(8) Emulsins.

Solid materials, such as whole organs and cellular matter, are preferably reduced in particle size such as by grinding, pulverizing or homogenization prior to application of the method of the invention to such materials.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in connection with the accompanying/drawings in which:

Figure 1:
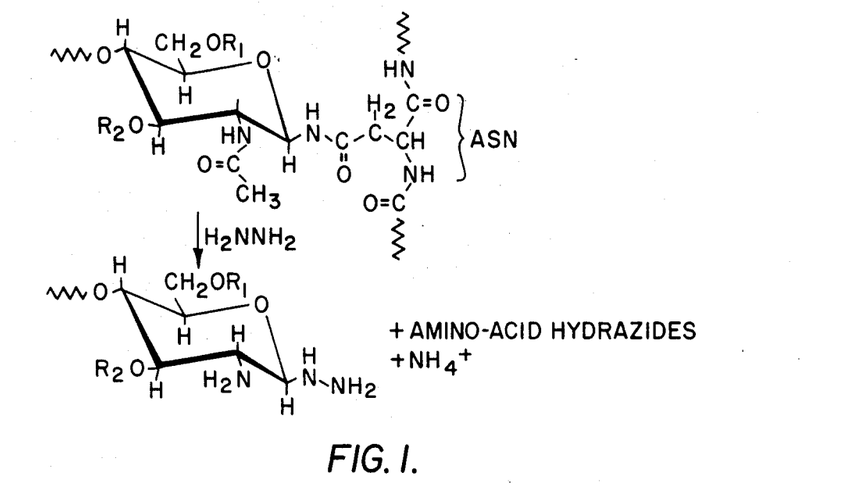
FIG. 1 shows partial chemical structures illustrating the hydrazinolysis reaction in which glycoprotein having a N-glycosyl linkage of oligosaccharide to asparagine (asn) is reacted with hydrazine to form a de-N-acetylated hydrazone derivative of the oligosaccharides, and amino acid hydrazides.
Figure 2:
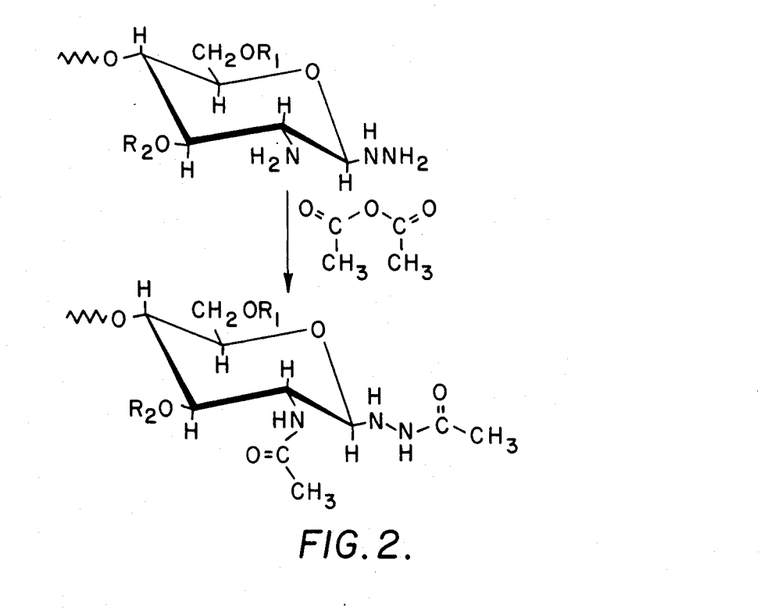
FIG. 2 illustrates the N-acetylation reaction in which the hydrazone derivative of the oligosaccharide of FIG. 1 is N-acetylated with acetic anhydride to form the N-acetylated hydrazone derivative of the oligosaccharide.
Figure 3:
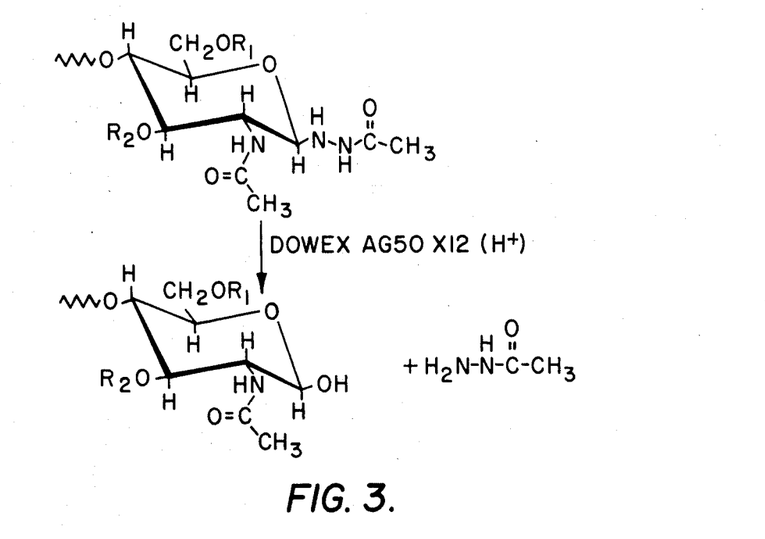
FIG. 3 illustrates the acid-catalysis process step in which the N-acetylated hydrazone derivative of oligosaccharide of FIG. 2 is contacted with an exchange resin (Dowex AG 50 X 12, H+) to replace Na+ with H+ ions and cleave acetylhydrazone groups, producing unreduced oligosaccharides.

The amino acid hydrazides shown in FIG. 1 are compounds of hydrazine and amino acid in which the —OH group of the α-carboxyl group of an amino acid is replaced with the hydrazino group —NHNH$_2$. The amino acid moieties of these compounds are contributed by the peptide portion of the glycoprotein. The hydrazides are contaminants which, in accordance with an important aspect of the invention, are removed by the cellulose column chromatography.

Preparatory to carrying out the hydrazinolysis of the glycoprotein or glycohormone starting material, the starting material is made essentially salt-free. The presence of salt is undesirable because of possible reaction with hydrazine to form hydrazine salts. Treatment of the glycoprotein or glycohormone is preferably carried out by exhaustively dialyzing against distilled water at about 4° C. with nitrogen purging.

In the hydrazinolysis reaction, it is important that the reaction be carried out under essentially water-free conditions; the presence of minor amounts of water is detrimental to the desired reaction to produce the de-N-acylated hydrazone derivative and reduces the yield obtained. Anhydrous reaction conditions can be achieved by use of anhydrous reactants and by carrying out the reaction in a moisture-free atmosphere of a sealed reaction vessel. Flame sealing of a glass reaction vessel under oxygen-free dry argon at atmospheric pressure is a preferred method of sealing.

The essentially water-free hydrazine can be prepared by freshly distilling a hydrazine/toluene mixture from CaO under an argon atmosphere.

Water can be removed from the glycoprotein or glycohormone by gentle drying methods such as by freeze-drying, lyophilization, subjecting to drying and dehydrating agents such as, for example, phosphorus pentoxide, or cryogenically drying over activated charcoal under reduced pressure.

The hydrazinolysis is carried out by heating the reaction mixture containing the glycoprotein or glycohormone from about room temperature (e.g., ca. 20°–25° C.) by gradually increasing the temperature during a preincubation step to about 65° C. and then maintaining the temperature to within a range of from about 65° to 100° C. Possible degradation at higher temperatures can occur; a preferred temperature is about 85° C., although a temperature of about 100° C. is suitable.

The time required to carry out the hydrazinolysis reaction can be from about 2 hours to 10 hours. These reaction times are not critical; possible degradation of the desired product may occur after prolonged reaction time.

In a preferred embodiment, the temperature is slowly raised through the reaction period, in the time range discussed above. For example the reaction temperature can be raised from room temperature to about 85° C. in increments of 10° C. per hour. It is believed that a gradual temperature increase helps to stabilize the oligosaccharides and produces a higher yield of the desired hydrazone derivative. The optimum time-temperature reaction conditions for a given glycoprotein or glycohormone wherein a mixture is obtained having as a major component the desired de-N-acetylated hydrazone derivative, can be easily determined by one skilled in the art.

Preferably from about 10 to about 50 mg of the glycoprotein or glycohormone material (dry weight) per ml of hydrazine are used in the hydrazinolysis reaction.

After completion of the hydrazinolysis reaction as can be determined analytically, unreacted hydrazine is removed such as by evaporation under reduced pressure. Evaporation under reduced pressure at 25° C. using liquid nitrogen and activated charcoal trapping followed by repetitive co-evaporation with anhydrous toluene is a preferred method of removing hydrazine.

The hydrazinolysis reaction cleaves the N-linked oligosaccharide structure of the glycoprotein or glycohormone, deacetylates the oligosaccharide, and donates a —NH$_2$ group to the released oligosaccharide. In addition, the hydrazine also reacts with a carbonyl group of the peptide linkage to form products including amino acid hydrazides.

Following the hydrazinolysis of the glycoprotein or glycohormone, the free amino groups of the de-N-acetylated hydrazone derivative of the oligosaccharide are N-acylated to convert the donated —NH$_2$ group to a desired N-acyl group and to convert the glucosamine residues to N-acylglucosamine residues. This N-acylation protects the reducing termini of the oligosaccharides from degradation during subsequent processing.

If it is desired to produce reduced oligosaccharides having at least one N-acetyl moiety present, as in the naturally occurring product, the N-acylation is carried out with an acetylating agent. A preferred acetylating agent is acetic anhydride.

In a preferred embodiment, the oligosaccharides are acetylated by reaction with excess acetic anhydride in saturated aqueous NaHCO$_3$ solution. Use of a several-fold molar excess of acetic anhydride over the total amount of amino groups in the hydrazinolate is preferred. A 5-fold molar excess is most preferred. Sequential acetylation at about 4° C. and then at about 20°–25° C. is a preferred method of N-acetylation.

Other suitable acylation reagents should be such as to permit the acyl moiety to serve as a leaving group.

After completion of the acylating step, to produce the N-acylated hydrazone derivative, the mixture containing this derivative is subjected to acid catalysis to cleave acylhydrazone and produce the unreduced oligosaccharide. Acid catalysis can be carried out by contacting the mixture with an acid such as sulfuric acid. However, in order to avoid cleavage of sialic acid, a preferred method of carrying out acid catalysis involves the use of strongly acidic cationic ion exchange resin. Use of a cation exchange resin on the H+ cycle will also serve to remove Na+ ions provided by the NaHCO$_3$.

A preferred cation ion exchange resin is Dowex® AG 50W X 12. This is an analytical grade, strongly acidic cation exchange resin composed of sulfonic acid functional groups attached to styrene/divinylbenzene copolymer lattice (12% crosslinkage). Other strongly acidic cation exchange resins can be similarly used.

Contaminants present in the mixture containing unreduced oligosaccharides include amino acid hydrazides formed by the initial hydrazinolysis reaction. These contaminants are removed in accordance with the invention by cellulose column chromatography. Preferably, the cellulose column employs a column of finely particulate or colloidal cellulose such as, for example, microcrystalline or microgranular cellulose. Fibrous cellulose is generally unsuitable. Microcrystalline celluloses are usually prepared from high purity cotton having a high alpha cellulose content, or other such plant sources of high purity cellulose. Methods of preparation are described by Battista, *Ind. Eng. Chem.* 42, 502 (1950); and U.S. Pat. Nos. 2,978,446 and 3,141,875. Preferred particle sizes can range from about <1 to about 100 microns. A typical microcrystalline cellulose is commercially available as Avicel® from FMC Corp., New York and E. Merck A.G., Darmstadt, West Germany.

The cellulose column chromatography preferably is carried out by washing a column of finely particulate cellulose successively with water, methanol transition solvent, and then an equilibration solvent of butanol, ethanol and water, followed by application of the N-acetylated oligosaccharide sample, and then extracting with the equilibration solvent followed by eluting successively with methanol transition solvent and water, in which the latter methanol and water washings are retained as the desired N-acetylated oligosaccharide fractions.

The proportions of the extraction solution components preferably are butanol:ethanol:water (4:1:1, respectively, by volume).

Prior to application of the extraction solution, the cellulose column is pretreated by washing successively with water and then methanol. Preferably, the cellulose column is extensively washed with distilled water and then with about one to two column volumes of methanol as a transition solvent.

Prior to application of the unreduced oligosaccharide sample, the cellulose column is equilibrated with the extraction solution. From about 5 to about 10 column volumes of the extraction solution are then used to extract the amino acid hydrazides.

The elution solutions are employed by using methanol as a transition solvent followed by water washing. Preferably, about one column volume of methanol and about 5 column volumes of distilled water are used for the elution.

A preferred bed volume of the cellulose can be calculated by the following formula:

Bed volume (mls)=[10+(10× material processed (gms)].

The recovered methanol and water fractions can be concentrated by freeze-drying or evaporation to remove solvent. The retained oligosaccharide preparation can be checked for peptide contamination by using $^1$H nuclear magnetic resonance spectroscopy and further purified, if necessary, by repeating the above cellulose column chromatography. For a general review of the application of $^1$H nuclear magnetic resonance spectroscopy, see R. A. Dwek, *Nuclear Magnetic Resonance (N.M.R.) in Biochemistry: Applications to Enzyme Systems*, Clarendon Press, Oxford, 1973; and Vliegenthart et al., *Adv. Carbohydr. Chem. & Biochem.* 41, Academic Press, 1983, p. 209.

The unreduced oligosaccharides also can be analyzed by high resolution gel permeation chromatography using a Bio-Gel® P-4 bead column. Bio-Gel P is prepared by copolymerization of acrylamide with N,N'-methylene bis-acrylamide. P-4 has an exclusion limit and fractionation range of 800-4000 daltons. It is a gel filtration material of choice due to its polyacrylamide structure. For a general review of analysis of oligosaccharides by gel filtration, see Yamashita et al., *Meth. Enzymol.* 83, Academic Press, 1982, pp. 105-126.

The following detailed examples will further illustrate the invention although it will be appreciated that the invention is not limited to these specific examples.

EXAMPLE 1

Isolation of Ovalbumin Oligosaccharides Method and Materials

Trypsin inhibitor type III-0 (ovalbumin) from chicken egg white was obtained from Sigma Chemical Co., St. Louis, Mo., Lot No: 128c - 8045. 2.5 grammes of the protein was exhaustively dialysed against distilled water at 4° C. The solution was freeze-dried, then dissolved in distilled water, placed in an acid washed 150 ml capacity hydrazinolysis tube and then freeze-dried. The freeze-dried material was further dried over phosphorous pentoxide under reduced pressure at room temperature for 7 days, and then cryogenically dried under reduced pressure (<10$^6$ bar) over activated charcoal (−196° C.) for a further 7 days.

Hydrazinolysis 20 ml freshly-distilled anhydrous hydrazine was added to the sample. The tube was sealed under anhydrous oxygen-free argon at atmospheric pressure and room temperature (ca. 20-25° C.) and then gradually heated to about 100° C. in increments of about 10° C. per hour. After heating the mixture for about 8.5 hours, the unreacted hydrazine was removed by rotary evaporation under reduced pressure and residual hydrazine was removed by repetitive co-evaporation with anhydrous toluene (5×3 ml).

Re-N-Acetylation

Re-N-acetylation was achieved using a five-fold excess of acetic anhydride over the number of moles of free amino groups. The residue was dissoved in 254 ml of a cold 0.5 molar solution of acetic anhydride (4° C.) in saturated aqueous sodium hydrogen carbonate, incubated for 10 min, and a further 13 ml of acetic anhydride was added, followed by a 50 minute incubation at 20° C., to produce the N-acetylated hydrazone derivative of oligosaccharide.

Acid Catalysis

The above mixture was then subjected to acid catalysis by the addition of 50 ml Dowex AG 50×12 (H+ form) and application of the sample to a 500 ml Dowex 50×12 (200–400 mesh) (H+) column to remove the Na+ ions present and to produce the unreduced oligosaccharide.

The column was washed with four column volumes of distilled water and the washings were combined and freeze-dried.

Column Purification

Contaminants were removed on a cellulose column as follows: Microcrystalline cellulose (E. Merck) was sized by sedimentation in distilled water and the fine particles discarded. The cellulose was poured into a 2.5×15 cm chromatography column and extensively washed with distilled water. The column was next washed with two column volumes of methanol and then two column volumes of butanol:ethanol:water 4:1:1 v/v (solvent I). The freeze-dried sample was dissolved in 25 ml water and 25 ml ethanol was added. 100 ml butanol was added to the top of the cellulose column and the sugar/water/ethanol mix was added to this. The top of the column was mixed thoroughly and then left for ten minutes before the liquid was allowed to flow through. The column was washed with five column volumes of solvent I, these washings were discarded. The column was next washed with one column volume of methanol followed by five column volumes of distilled water. These washings (water and methanol) were collected and concentrated by rotory evaporation, filtered (0.2 $\mu$M Teflon ® membrane), followed by lyophilization.

Figure 4:
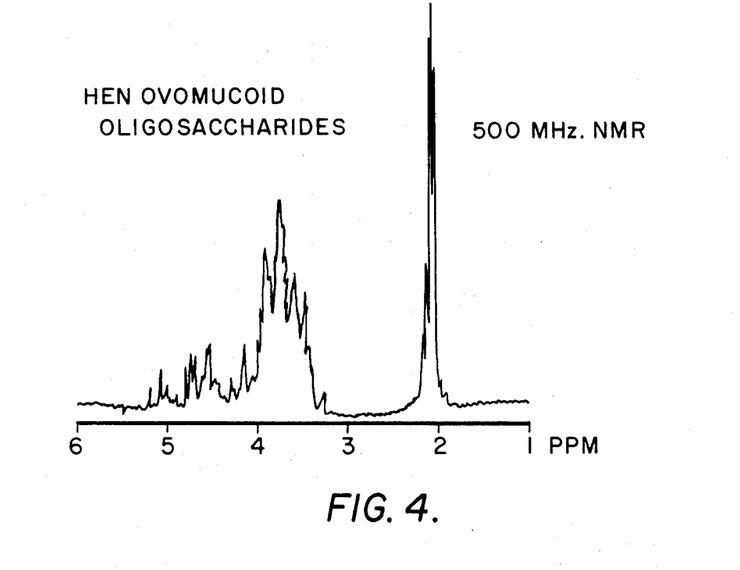
FIG. 4 shows the $^1$H 500 MHz NMR spectrum of the oligosaccharides released from trypsin inhibitor type III-0: chicken egg white purified ovomucoid in one embodiment of the invention.

The unreduced oligosaccharide fraction was shown by $^1$H NMR (FIG. 4) to be essentially free of contaminants and to consist of high purity unreduced oligosaccharides. The oligosaccharide sample was stored at $-20°$ C.

EXAMPLE 2

Isolation of Fetuin Oligosaccharides Method and Materials

Fetuin from fetal calf serum Type III was obtained from Sigma Chemical Co., St. Louis, Mo., F-2379, Lot No: 53F-9630. 5 grammes of the protein was exhaustively dialysed against distilled water at 4° C. The solution was freeze-dried, then dissolved in distilled water, placed into an acid washed 150 ml capacity hydrazinolysis tube and then freeze-dried. The sample was cryogenically dried over activated charcoal ($-196°$ C.) for 14 days under reduced pressure ($<10^6$ bar).

Hydrazinolysis 35 ml freshly-distilled anhydrous hydrazine was added to the sample. The tube was sealed under anhydrous oxygen-free argon at atmospheric pressure, and incubated for 7.5 hours at 100° C. After incubation, unreacted hydrazine was removed by rotary evaporation under reduced pressure and residual hydrazine was removed by repetive co-evaporation with anhydrous toluene (7×5 ml).

Re N-Acetylation

Re-N-acetylation was achieved using a five-fold excess of acetic anhydride over the number of moles of free amino groups. The residue was dissolved in 500 ml of a cold 0.5 molar solution of acetic anhydride (4° C.) in saturated aqueous sodium hydrogen carbonate, incubated for 10 min, and a further 26 ml of acetic anhydride was added, followed by a 50 minute incubation at 20° C.

Acid Catalysis

The above mixture was then subjected to acid catalysis by the addition of 100 ml Dowex AG 50×12 (H+ form) and application of the sample to a one liter Dowex AG 50×12 (200–400 mesh) (H+) column, to remove the Na+ ions present and to produce the unreduced oligosaccharide.

The column was washed with three column volumes of distilled water and the washings were combined and freeze-dried.

Column Purification

Contaminants were removed on a cellulose column as follows: Microcrystalline cellulose was sized by sedimentation in distilled water and the fine particles discarded. The cellulose was poured into a 2.5×15 cm chromatography column and extensively washed with distilled water. The column was next washed with two column volumes of methanol and then two column volumes of butanol: ethanol:water 4:1:1 v/v (solvent I). The freeze-dried sample was dissolved in 50 ml water and 50 ml ethanol was added. 200 ml butanol was added to the top of the cellulose column and the sugar/water/ethanol mix was added to this. The top of the column was mixed thoroughly and then left for ten minutes before the liquid was allowed to flow through. The column was washed with ten column volumes of solvent I, these washings were discarded. The column was next washed with one column volume of methanol followed by four column volumes of distilled water. These washings (water and methanol) were collected, concentrated by rotary evaporation, filtered (0.2 $\mu$M Teflon membrane), followed by lyophilization.

Figure 5:
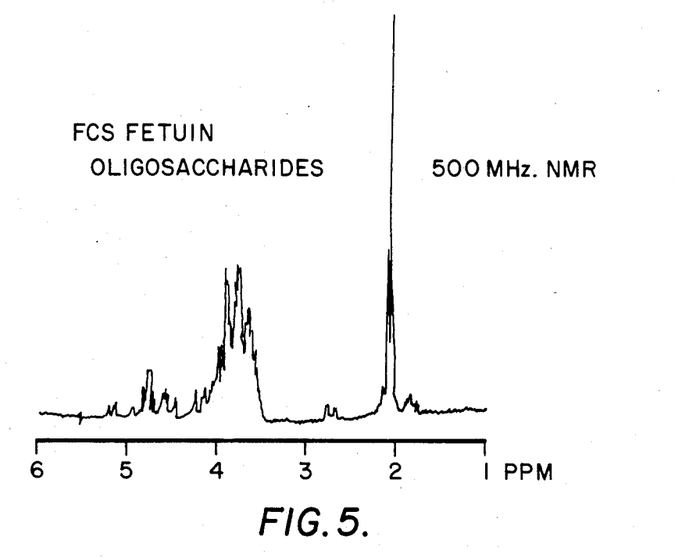
FIG. 5 shows the $^1$H 500 MHz NMR spectrum of the oligosaccharides released from fetuin type III from fetal calf serum in another embodiment of the invention.

The unreduced oligosaccharide fraction was shown by $^1$H NMR (FIG. 5) to be essentially free of contaminants and to consist of high purity unreduced oligosaccharides. The oligosaccharide fraction was stored at $-20°$ C.

EXAMPLE 3

Isolation of Transferrin Oligosaccharides Method and Materials

Human Serum Transferrin was obtained from Sigma Chemical Co., St. Louis, Mo., Lot No: 93F-0195. 5 grammes of the protein was exhaustively dialysed against distilled water at 4° C. The solution was freeze-dried, dissolved in distilled water, placed into an acid washed 150 ml capacity hydrazinolysis tube and freeze-dried.

The sample was dried over phosphorous pentoxide under reduced pressure at room temperature for 2 days, and then cryogenically dried under reduced pressure ($<10^6$ bar) over activated charcoal ($-196°$ C.) for a further 14 days.

Hydrazinolysis 35 ml freshly-distilled anhydrous hydrazine was added to the sample. The tube was sealed under anhydrous oxygen-free argon at atmospheric pressure, and incubated for 7.5 hours at 100° C. After incubation, unreacted hydrazine was removed by rotary evaporation under reduced pressure and repetitive co-evaporation with anhydrous toluene (8×5 ml).

Re-N-Acetylation

Re-N-acetylation was achieved using a five-fold excess of acetic anhydride over the number of moles of free amino groups. The residue was dissolved in 500 ml of a cold 0.5 molar solution of acetic anhydride (4° C.) in saturated aqueous sodium hydrogen carbonate, incubated for 10 min, and a further 26 ml of acetic anhydride was added, followed by a 50 minute incubation at 25° C.

Acid Catalysis

The above mixture was then subjected to acid catalysis by the addition of 100 ml Dowex AG 50×12 (H+ form) and application of the sample to a one liter Dowex AG 50×12 (H+) 200-400 mesh column.

The column was washed with three column volumes of distilled water and the washings combined and freeze-dried.

Column Purification

Contaminants were removed on a cellulose column as follows: Microcrystalline cellulose was sized by sedimentation in distilled water and the fine particles discarded. The cellulose was poured into a 2.5×15 cm chromatography column and extensively washed with distilled water. The column was next washed with two column volumes of methanol and then two column volumes of butanol: ethanol:water 4:1:1 v/v (solvent I). The freeze-dried sample was dissolved in 50 ml water and 50 ml ethanol was added. 200 ml butanol was added to the top of the cellulose column and the sugar/water-/ethanol mix was added to this. The top of the column was mixed thoroughly and then left for ten minutes before the liquid was allowed to flow through. The column was washed with ten column volumes of solvent I, these washings were discarded. The column was next washed with one column volume of methanol followed by five column volumes of distilled water. These washings (water and methanol) were collected and concentrated by rotary evaporation, filtered (0.2 µM Teflon membrane) followed by lyophilization.

Figure 6:
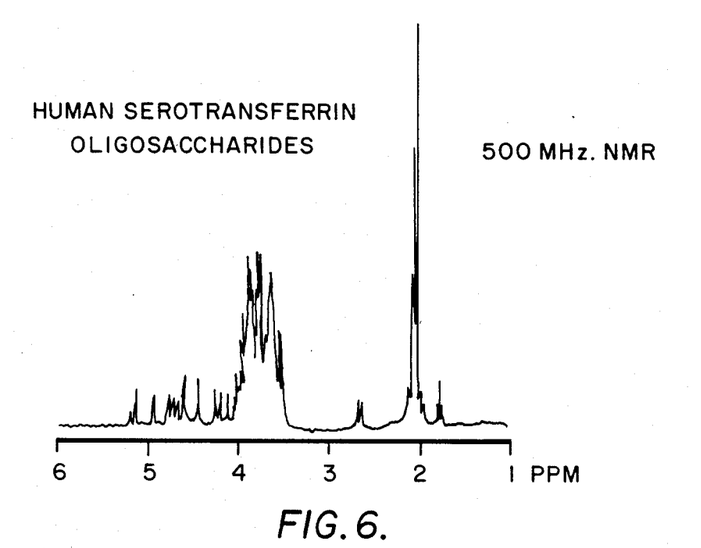
FIG. 6 shows the $^1$H 500 MHz NMR spectrum of the oligosaccharides released from human serum transferrin in still another embodiment of the invention.

The unreduced oligosaccharide fraction was shown by $^1$H NMR (FIG. 6) to be essentially free of contaminants, and was stored at −20° C.

| Summary of Yields of Examples 1-3: | | | |
|---|---|---|---|
| Example | Total Protein | Dry weight oligosaccharides recovered | % Carbohydrate by weight recovered |
| (1) Ovomucoid | 2.5 gram | 670 mg | 26% (25-30%)* |
| (2) Fetuin | 5.0 gram | 663 mg | 13.3% (16%)* |
| (3) Transferrin | 5.0 gram | 287 mg | 5.7% (5.6%)* |

*Theoretical recovery

EXAMPLE 4

Large-Scale Isolation of Unreduced Oligosaccharides from whole Human Parotid Gland (1) Human parotid glands were excised from recent cadavers and frozen (−20° C.).

(2) 100 g of the frozen tissue was sliced thinly, frozen in liquid nitrogen, pulverized using a mortar and pestle and lyophilized.

(3) The material was then washed extensively with anhydrous acetone at −10° C.

(4) Glycoprotein was extracted by homogenizing the sample in 1 liter of 0.01 M Tris-HCl/0.1 M NaCl (pH 7.7) at 4° C.

(5) The homogenate was centrifuged at 600×g for 15 min, then the supernatant collected and exhaustively dialysed against distilled water at 4° C.

(6) The sample was freeze-dried, then placed in a 150 ml capacity hydrazinolysis tube and cryogenically dried for 14 days.

(7) The dried sample was dissolved in 20 ml freshly distilled anhydrous hydrazine and the tube sealed under dry oxygen-free argon at 1 atmosphere pressure.

(8) The sample was incubated at 100° C. for 7 hours.

(9) After re-opening of the tube under a dry argon atmosphere the unreacted hydrazine was removed by evaporation under reduced pressure at 30° C. Trace residual hydrazine was removed by coevaporation with anhydrous toluene (7×5 ml toluene).

(10) The sample was re-N-acetylated as follows:

(a) The dried sample was dissolved in 250 ml 0.5 M acetic anhydride in saturated aqueous NaHCO$_3$ (4° C.). After 10 minutes incubation at 4° C. a further 10 ml of 10 M acetic anhydride was added and incubation was continued for 60 minutes at 20° C.

(b) Na+ ions were removed and unreduced oligosaccharides were produced by ion exchange chromatography using a 1000 ml Dowex AG 50W×12 (H+) column, the sample being eluted off with 5 column volumes of water.

(11) After freeze-drying, non-carbohydrate contaminants were removed by cellulose column chromatography. The sample was applied to a 30 ml microcrystalline cellulose column previously equilibrated in butanol:ethanol:water (4:1:1 v/v) and washed with 10 columns of butanol: ethanol:water (4:1:1, v/v). The carbohydrate was eluted with 5 column volumes of water using 1 column volume of methanol as a transition solvent.

Figure 7:
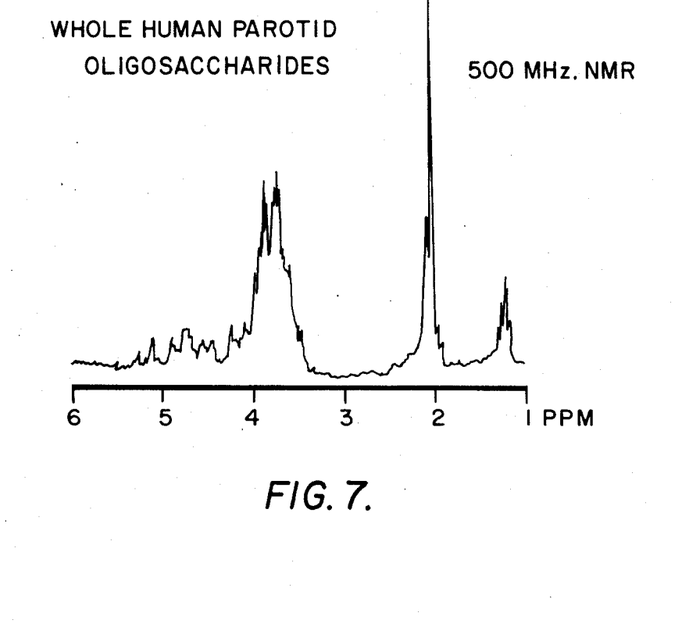
FIG. 7 shows the $^1$H 500 MHz NMR spectrum of the oligosaccharides released from whole human parotid gland in yet another embodiment of the invention.

(12) After drying by rotary evaporation followed by lyophilization, the material (160 mg) was examined by 300 MHz $^1$H nuclear magnetic resonance spectroscopy (FIG. 7) and shown to be high purity unreduced oligosaccharides free of peptide contaminants.

Various other examples will be apparent to the person skilled in the art after reading the present disclosure without departing from the spirit and scope of the invention and it is intended that all such other examples be included within the scope of the appended claims.

What is claimed is:

1. A method for isolating unreduced oligosaccharides from a glycoprotein or glycohormone having an N-linked oligosaccharide structure comprising the steps of:

(a) hydrazinolyzing the glycoprotein or glycohormone by heating an essentially water-free and essentially salt-free glycoprotein or glycohormone in the presence of essentially water-free hydrazine under reaction conditions sufficient to cause cleavage at the N-linked sites to produce a mixture having as a major component a de-N-acetylated hydrazone derivative of an oligosaccharide;

(b) N-acylating the hydrazone derivative of (a) with acylating agent to form a N-acylated hydrazone derivative of said oligosaccharide;

(c) subjecting the hydrazone derivative of (b) to acid catalysis to produce said unreduced oligosaccharides; and (d) subjecting the unreduced oligosaccharides of (c) to cellulose column chromatography to remove contaminants and recover therefrom said unreduced oligosaccharides.

2. The method of claim 1 wherein the hydrazinolysis is carried out by heating gradually from an initial temperature of about room temperature to a range of from about 65° to 100° C., over a period of from about 2 to 10 hours.

3. The method of claim 1 in which the N-acylating agent is acetic anhydride.

4. The method of claim 1 wherein the acid catalysis is carried out by use of a strongly acidic cationic ion exchange resin.

5. The method of claim 4 wherein the cation ion exchange resin is a cross-linked styrene/divinylbenzene resin with sulfonic acid functional groups.

6. The method of claim 1 wherein the cellulose column is microcrystalline cellulose.

7. The method of claim 1 in which the cellulose column chromatography is carried out by washing with an extraction solution of butanol:ethanol:water to remove contaminants, followed by washing with elution solutions of methanol and water to obtain said unreduced oligosaccharides.

8. The method of claim 7 in which the extraction solution components of butanol:ethanol:water are applied to the cellulose column, respectively, in proportions of about 4:1:1, volume/volume.

9. The method of claim 7 in which from about 5 to about 10 column volumes of the extraction solution are applied to the cellulose column to remove the contaminants.

10. The method of claim 7 in which about one column volume of methanol followed by about 5 column volumes of distilled water are applied to the cellulose column to elute said unreduced oligosaccharides.

11. A method for isolating unreduced oligosaccharides from a glycoprotein or glycohormone having an N-lined oligosaccharide structure comprising the steps of:
(a) hydrazinolyzing the glycoprotein or glycohormone by heating an essentially water-free and essentially salt-free glycoprotein or glycohormone in the presence of essentially water-free hydrazine to a temperature in the range from about 65° C. to 100° C. for a reaction time of from about 2 to 10 hours, to cause cleavage at the N-linked sites to produce a mixture having as a major component a de-N-acetylated hydrazone derivative of an oligosaccharide;
(b) N-acetylating the hydrazone derivative of (a) with excess acetic anhydride in the presence of saturated NaHCO$_3$ solution at an initial reaction temperature of about 4° C. and increasing the reaction temperature to about 20°-25° C. to form a N-acetylated hydrazone derivative of said oligosaccharide;
(c) subjecting the hydrazone dervative of (b) to acid catalysis by contacting said mixture with an acidic cationic exchange resin of cross-linked styrene/divinylbenzene having sulfonic acid functional groups, to replace Na$^+$ ions with H$^+$ ions and to produce said unreduced oligosaccharides; and
(d) subjecting the resulting unreduced oligosaccharides of (c) to cellulose column chromatography by washing with an extraction solution of butanol:ethanol:water to remove contaminants, followed by washing with elution solutions of methanol and water to recover said unreduced oligosaccharides.

12. The method of claim 11 wherein the hydrazinolysis is carried out by heating gradually from an initial temperature of about room temperature in increments of about 10° C. per hour.

13. The method of claim 11 wherein the cellulose column is microcrystalline cellulose.

14. The method of claim 11 in which the extraction solution components of butanol:ethanol:water are applied to the cellulose column, respectively, in proportions of about 4:1:1, volume/volume.

15. The method of claim 11 in which from about 5 to about 10 column volumes of the extraction solution are applied to the cellulose column to remove contaminants.

16. The method of claim 11 in which about one column volume of methanol followed by about 5 column volumes of distilled water are applied to the cellulose column to elute said unreduced oligosaccharides.

17. The method of claim 16 in which about one column volume of methanol followed by about 5 column volumes of distilled water are applied to the cellulose column to elute the said unreduced oligosaccharides.

* * * * *